US00PP07839P

United States Patent [19]

Kientzler

[11] Patent Number: Plant 7,839

[45] Date of Patent: Mar. 24, 1992

[54] NEW GUINEA IMPATIENS PLANT NAMED SATURNIA

[75] Inventor: Ludwig Kientzler, Gensingen, Fed. Rep. of Germany

[73] Assignee: Paul Ecke Ranch, Inc., Encinitas, Calif.

[21] Appl. No.: 577,134

[22] Filed: Sep. 5, 1990

[51] Int. Cl.[5] ..... A01H 5/00

[52] U.S. Cl. ..... Plt./68

[58] Field of Search ..... Plt./68, 87.6

*Primary Examiner*—Howard J. Locker

*Attorney, Agent, or Firm*—Foley & Lardner

[57] ABSTRACT

An Impatiens plant named Saturnia having lavender flowers which are slightly cupped in form, glossy dark green foliage, vigorous growth habit, and excellent self-branching.

1 Drawing Sheet

The present invention relates to a new and distinctive cultivar of impatiens plant known by the cultivar name Saturnia, botanically known as Impatiens, and commercially known as New Guinea Impatiens.

Saturnia was developed by the applicant through a controlled breeding program in Gensingen, Federal Republic of Germany. The male or pollen parent was identified by the cultivar designation A 720, and the female or seed parent was identified by the cultivar designation B 2880. Saturnia was discovered and selected as one flowering plant within the progeny of the cross by the applicant in a controlled environment in Gensingen, Federal Republic of Germany.

The first act of asexual reproduction of Saturnia was accomplished when terminal or stem cuttings were taken from the initial selection by applicant in a controlled environment in Gensingen, Federal Republic of Germany. Horticultural examination of selected plants of Saturnia has demonstrated that the combination of characteristics as herein disclosed for Saturnia are firmly fixed and are retained through successive generations of asexual reproduction.

Saturnia has not been observed under all possible environmental conditions. The phenotype may vary significantly with variations in environment such as temperature, light intensity, soil conditions, nutrient feeding, and day length.

The following characteristics distinguish the new Impatiens from both its parent varieties and other cultivated impatiens of this type known and used in the floriculture industry within the knowledge of applicant:

1. Lavender flowers which are slightly cup shaped in form.
2. Glossy dark green foliage. The contrast of colors of the foliage and flowers is striking.
3. Vigorous growth habit.
4. Excellent self-branching.

The accompanying colored photograph illustrates in perspective view the overall appearance of this cultivar, with colors being as true as it is reasonably possible to obtain in a colored reproduction of this type.

The following is a detailed description of Saturnia based on plants produced under commercial practice in Encinitas, Calif. Unrooted cuttings were rooted under intermittent mist, and the plants subsequently transplanted to 15 cm. pots. Flowering commenced in November 1989. Cuttings were taken from these established plants in January 1990, rooted and planted in 10 cm. pots. After 5-6 more weeks the plants were nicely proportioned for 10 cm. pots, and data was collected. Most of the data which follows was collected between Apr. 1-15, 1990 in Encinitas, Calif. The measurements and description of foliage were taken from fully expanded leaves.

Color references are made to the Royal Horticultural Society Colour Chart except where general terms of ordinary dictionary significance are used. Color chart correlations were made under indirect natural light conditions, with the leaves and flowers being compared to the R.H.S. Colour Chart on a north exposure.

Parentage: Seedling from cross pollination of male parent A 720 with female parent B 2880.

Propagation:

*Type cutting.*—Tip cutting. Stems 2-3 cm. long will develop to 4-5 cm. after 21 days in propagation.

*Time to initiate roots.*—8-10 days at 23° C. Nicely developed root mass in 18-21 days.

*Rooting habit.*—Numerous, fibrous adventitious roots from the stem.

Plant description:

*Form.*—Symmetrical, bush shaped, flowering herb, with self-branching characteristics giving the plant a full appearance.

*Habit of growth.*—Self-branching, vigorous habit, producing whorls of leaves and flowers on branched stems. Growth is indeterminate and flowering is continuous.

*Size.*—When grown as single plants in 10 cm pots with the plants not being pinched, plants in full flower are 32-34 cm in height (including the pot), 29-31 cm in width or spread, and have an average number of 9 strong branches.

*Foliage description.*—Leaves are simple. Lower leaves on stem are opposite. Higher leaves in whorls of 3 to 5. Leaf shape: Mostly ovate to somewhat elliptic. Leaf blade size: 7-8 cm.×3-4 cm. Leaf margin: Ciliated. Leaf texture: Somewhat undulant. (a) Upper surface: Glabrous. (b) Under surface: Glabrous. Leaf color: Dark green. (a) Upper surface: Green, darker than RHS 139A. (b) Under surface: Green with grayed-purple near RHS 184A. Venation: Pinnate with red mid-vein.

Flowering description:

*Flowering habit.*—Very floriferous, flowering continuously. Flowers develop progressively around the whorl of leaves, taking 5–7 days from buds which show color to bloom. Flowers are single and large, lasting for 2–3 weeks.

*Natural flowering season.*—Flowering is indeterminate and occurs throughout the year. Quantity of flowers increases with increasing light intensity and duration.

*Flower buds.*—Ellipsoidal and covered with 5 sepals. A green spur, approximately 5 to 5.5 cm. long originates from the base of the major sepal. Two very small sepals on either side of the spurred sepal and two additional, rudimentary sepals are fused to back of the top petal.

*Flowers borne.*—Singly, on pedicels 3.5 cm. long and green in color.

*Quantity of flowers.*—Floriferous, with one flower per leaf occurring progressively around the whorl of leaves so that tight buds to mature blooms are visible at the same time in large numbers.

*Petals.*—Number of petals: Five (5). Shape: Top petal heart shaped with wide base, all other petals heart shaped with pointed base. All petals overlap. The flower presentation is slightly cup shaped. Color: Lavender. Upper surface: Darker than RHS 77C, near RHS 77B. Each petal has a very light area 56D to almost white at the petal base and radiating outwardly about 1 cm, with these light areas collectively defining a light "eye" in the center of the flower. Under surface: Near RHS 77C. Size of flowers: 4–5 cm. diameter.

*Reproductive organs.*—Stamens: Five (5), with the lower stamen being shorter than the other stamens. Stamens are united in an asymmetrical tube surrounding the ovary. Anthers: Hooded, cream fused with red. Pollen: Cream color. Stigma: Five pointed star, creamy white. Styles: Very short, reddish in color. Ovary: 5 celled, 4 mm. long until fertilized, green in color.

I claim:

1. A new and distinct cultivar of Impatiens plant named Saturnia, as illustrated and described.

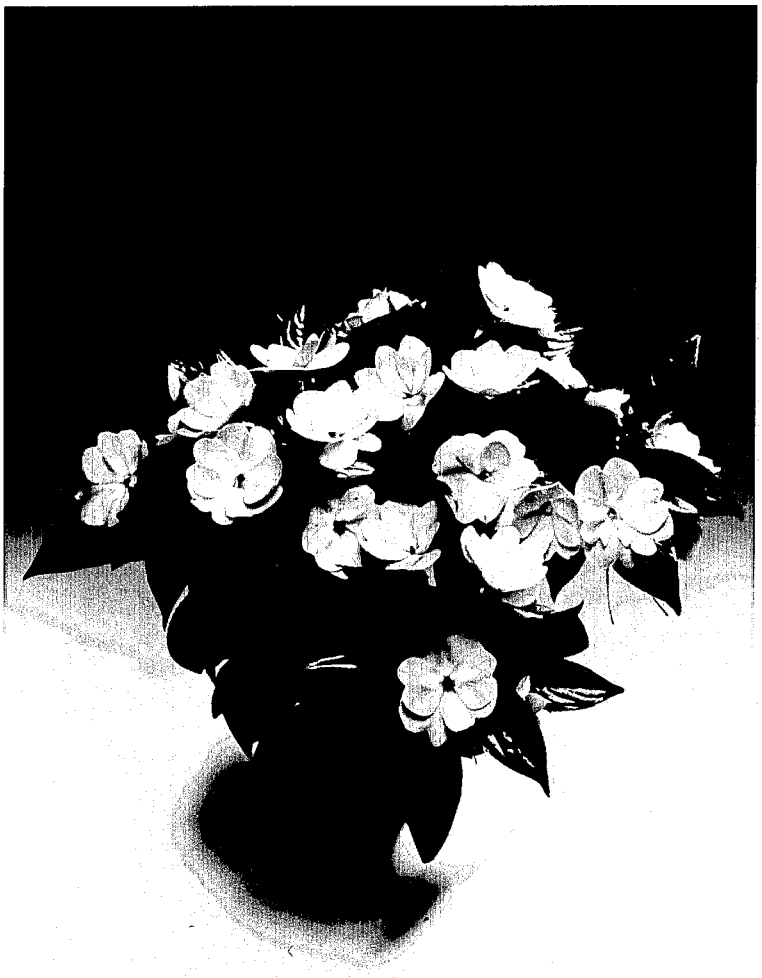

* * * * *